United States Patent [19]  
Andrews

[11] 4,212,988  
[45] Jul. 15, 1980

[54] PREPARATION OF 2-KETOGULONIC ACID

[75] Inventor: Glenn C. Andrews, Waterford, Conn.

[73] Assignee: Pfizer Inc., NY

[21] Appl. No.: 24,284

[22] Filed: Mar. 26, 1979

Related U.S. Application Data

[63] Continuation-in-part of Ser. No. 965,626, Dec. 1, 1978, abandoned.

[51] Int. Cl.² ............... C07C 59/33; C07C 67/30; C07C 69/61
[52] U.S. Cl. .................. 560/174; 260/343.7; 260/501.15; 562/577
[58] Field of Search ............ 560/174; 562/577; 260/501.15

[56] References Cited

U.S. PATENT DOCUMENTS

| | | |
|---|---|---|
| 2,153,311 | 4/1939 | Pasternack et al. ............ 560/174 |
| 2,207,991 | 7/1940 | Pasternack et al. ............ 560/174 |
| 2,301,811 | 11/1942 | Reichstein ..................... 562/577 |
| 2,444,885 | 7/1948 | Van der Laan ................. 560/174 |
| 2,847,421 | 8/1958 | D'Addieco ..................... 562/577 |
| 2,853,495 | 9/1958 | Ruskin et al. .................. 562/577 |
| 3,922,194 | 11/1975 | Sonoyama et al. ............. 195/30 |

OTHER PUBLICATIONS

Lane, Aldrichimica, 6, 61 (1973).  
Kelly et al., J.A.C.S., 86, 3882 (1964).  
White et al., J.A.C.S., 90, 2009 (1968).  
Ibid, 92, 4203 (1970).

Primary Examiner—Vivian Garner  
Attorney, Agent, or Firm—Francis X. Murphy; Charles J. Knuth; Peter C. Richardson

[57] ABSTRACT

2,5-Diketogluconic acid, alkyl esters or salts thereof, are reduced by an amine-borane to 2-ketogulonic acid, an intermediate for the preparation of ascorbic acid.

16 Claims, No Drawings

PREPARATION OF 2-KETOGULONIC ACID

CROSS REFERENCE TO RELATED APPLICATION

This application is a continuation-in-part of copending U.S. Pat. application Ser. No. 965,626, filed Dec. 1, 1978, now abandoned.

BACKGROUND OF THE INVENTION

This invention relates to a process for preparing 2-ketogulonic acid, its alkyl esters and salts by the selective reduction of 2,5-diketogluconic acid, alkyl esters or salts thereof. 2-ketogulonic acid is useful as an intermediate for the preparation of ascorbic acid.

The complete reduction of 2,5-diketogluconic acid with an excess of sodium borohydride has been reported as part of a structural determination of the acid, see Agr. Biol. Chem. 28, 819 (1964), J. Biol. Chem. 204, 34 (1953) and Antonie Van Leeuwenhoeck 37, 185 (1971). The catalytic reduction of 2,5-diketogluconic acid using a Raney nickel catalyst and hydrogen gives a low yield of a mixture of 2-ketogluconic acid and 2-ketogulonic acid, with 2-ketogluconic acid being the major product, Agr. Biol. Chem. 28, 819 (1964). Applicant's copending U.S. Patent application Ser. No. 843,946 filed Dec. 10, 1977, U.S. Pat. No. 4,159,990, discloses a process for the reduction of a 2,5-diketogluconate with one equivalent of an alkali metal borohydride to form a mixture of 2-ketogulonic acid and 2-ketogluconic acid.

It has now been found that a 2,5-diketogluconate can be reduced with greater regioselectivity and stereoselectivity, thereby giving higher yields of the desired 2-ketogulonic acid for subsequent conversion to ascorbic acid, by use of an amine-borane reducing agent at a pH between about 2 and 7. Thus, for example yields of 2-ketogulonic acid and 2-ketogluconic acid of 94% or higher, with about 96% of the product mixture being the desired 2-ketogulonic acid, may be obtained by this process. These higher yields can be obtained without conducting the reduction reaction in the presence of a boron-complexing agent as is required for optimum yields in the alkali metal borohydride reduction. It has also been found that 2-ketogulonic acid formed by this process is not subject to further reduction, i.e., reduction of the 2-keto group, at a reasonable rate even in the presence of excess amine-borane reducing agent. The 2-keto group of 2-ketogulonic acid is, however, rapidly reduced by an alkali metal borohydride, resulting in less than optimum yields of 2-ketogulonic acid when formed by the alkali metal borohydride reduction of a 2,5-diketogluconate and precluding the use of excess alkali metal borohydride to increase rates of reduction and conversions of the 2,5-diketogluconate starting material. Further, the 2,5-diketogluconate is most stable under the acidic conditions employed in the present amine-borane reduction.

SUMMARY OF THE INVENTION

The present invention relates to a process for preparing a 2-ketogulonate which comprises reducing a 2,5-diketogluconate with an amine-borane of the formula $R_1R_2HN.BH_3$ or with pyridine-borane in solution at a pH between about 2 and 7 at a temperature between about $-20°$ to $70°$ C., wherein $R_1$ and $R_2$ are each selected from hydrogen and alkyl of 1 to 4 carbon atoms; and said 2,5-diketogluconate is selected from 2,5-diketogluconic acid, a normal alkyl ester of said acid wherein said alkyl group is of 1 to 4 carbon atoms, and the salt of said acid having a counterion selected from an alkali metal, an alkaline earth metal, ammonium and tetraalkyl-ammonium having from 1 to 4 carbon atoms in each alkyl group.

Preferred amine-borane reducing agents of the formula $R_1R_2HN.BH_3$ include ammonia-borane, methylamine-borane, dimethylamine-borane, and t-butylamine-borane. Pyridine-borane is also a preferred amine-borane.

The reaction is preferably conducted at temperatures in the range $0°-25°$ C., preferably at a pH in the range 4 to 6. Preferred 2,5-diketogluconate starting materials include 2,5-diketogluconic acid, sodium 2,5-diketogluconate, calcium 2,5-diketogluconate and methyl 2,5-diketogluconate.

DETAILED DESCRIPTION OF THE INVENTION

The present process provides for the regioselective and stereoselective reduction of a 2,5-diketogluconate with an amine-borane. The reaction product is predominantly a 2-ketogulonate, with only minor amounts, about 2 to 12%, of a 2-ketogluconate being formed. The reaction product is therefore suitable for the preparation of ascorbic acid by means known in the art, for example the base catalyzed lactonization of the lower alkyl esters of 2-ketogulonic acid. If desired, the minor amounts of 2-ketogluconic acid present in the reaction product may be converted to erythorbic acid by similar methods, either separately or concurrently with the conversion of the 2-ketogulonate to ascorbic acid.

The 2,5-diketogluconate used as the starting material in the present invention may be either 2,5-diketogluconic acid or salts of the acid. Suitable salts include those having as counterions an alkali metal, an alkaline earth metal, ammonium and tetra-alkylammonium where the alkyl groups have from 1 to 4 carbon atoms. Also useful as starting materials for the present process are the normal alkyl esters of 2,5-diketogluconic acid wherein the alkyl group is of 1 to 4 carbon atoms. As used in the specification and claims hereof, the terms 2,5-diketogluconate, 2-ketogulonate and 2-ketogluconate include the free acids and suitable alkyl esters and salts thereof as previously described. The 2,5-diketogluconic acid and salts thereof may be produced by any means known in the art. Generally, the 2,5-diketogluconate is produced as the calcium salt in aqueous solution by fermentation using methods well known in the fermentation industry and may be used directly in this form as the starting material for the present process. The 2,5-diketogluconate can also be produced by fermentation in the presence of other ions such as sodium and the resulting sodium 2,5-diketogluconate may likewise be used directly in the present process. In an alternative method, the 2,5-diketogluconate is prepared in the conventional way as the calcium 2,5-diketogluconate and converted to the desired compound by addition of a salt effective to precipitate calcium and leave the 2,5-diketogluconate in solution with the desired counterion. Thus for example sodium or ammonium 2,5-diketogluconate can be produced by addition of sodium or ammonium carbonate, respectively, to a solution of calcium 2,5-diketogluconate produced by fermentation. Calcium is precipitated as calcium carbonate leaving the 2,5-diketogluconate in solution with sodium or ammonium counterions. The free acid may also be neutralized with an appropriate hydroxide or other salt. If desired, the 2,5-diketogluconate can be isolated, purified and redissolved.

The normal alkyl esters of 2,5-diketogluconic acid wherein alkyl is of 1 to 4 carbon atoms may be prepared by heating a solution of 2,5-diketogluconic acid or a suitable salt thereof in the appropriate normal alkanol at 50° C. to 100° C. in the presence of a catalytic amount of a strong acid, such as concentrated sulfuric acid, hydrochloric acid, p-toluene sulfonic acid and the like, to form the corresponding alkyl 2,5-diketogluconate-5,5-dialkyl acetal. Salts of 2,5-diketogluconic acid suitable for preparation of the esters by this means include the alkali metal, alkaline earth metal, ammonium and tetraalkyl ammonium salts, wherein each alkyl group of the tetraalkyl ammonium ion has from 1 to 4 carbon atoms. The acetal is then hydrolyzed with aqueous acid at a temperature between about $-10°$ C. and 30° C. to afford the desired alkyl ester of 2,5-diketogluconic acid. Suitable acids include aqueous hydrochloric acid, trifluoroacetic acid, sulfuric acid, sulfonic acid ion exchange resins and the like.

When an alkali metal 2,5-diketogluconate is utilized as the starting material in the present amine-borane reduction process, the sodium salt is preferred. A preferred alkaline earth 2,5-diketogluconate is the calcium salt. When tetraalkyl ammonium salts are employed, the tetramethylammonium salt is preferred. A preferred alkyl ester starting material is methyl 2,5-diketogluconate.

The reduction of the 2,5-diketogluconate is effected by contacting a solution of the 2,5-diketogluconate with an effective amount of an amine-borane of the formula $R_1R_2HN \cdot BH_3$ wherein $R_1$ and $R_2$ are as previously defined, or with pyridine-borane. Preferably, the reaction is effected in aqueous solution, optionally containing organic cosolvents such as, but not limited to, alkanols of 1 to 4 carbon atoms, alkanediols of 2 to 4 carbon atoms, and the like. Methanol is a preferred cosolvent. The concentration of the 2,5-diketogluconate is not critical but is preferably between about 5 and 20 weight percent. The concentration of the 2,5-diketogluconate formed by fermentation is generally within this range and thereby provides a suitable aqueous solution of the starting material for use in the present process. When an alkyl ester is utilized as starting material, the reaction may be conducted in anhydrous solvents, such as alkanols, especially methanol. In all cases, it is not necessry that all the 2,5-diketogluconate be dissolved in the solvent, provided a substantial part of the material of the starting material is in solution.

The amine-boranes useful as reducing agents in the present process are well known in the art and are generally commercially available, see for example C. F. Lane, Aldrichimica 6, 51 (1973). If desired, they can be prepared by known methods, for example by the reaction of diborane with an appropriate amine of the formula $R_1R_2NH$ to form the amine-borane $R_1R_2HN \cdot BH_3$, the reaction generally being conducted at temperatures of about 0° C. or below.

The amount of amine-borane employed in the reduction reaction will determine the amount of 2,5-diketogluconate starting material present in the reaction mixture that will be converted to the desired reaction product. Preferably, sufficient amine-borane will be employed to convert all of the 2,5-diketogluconate starting material present in the reaction mixture, since this will give optimum yields of the desired 2-ketogulonate suitable for subsequent conversion to ascorbic acid. However, if desired lesser amounts of the amine-borane reducing agent can be used to achieve lower conversions, i.e., reduction of only a part of the 2,5-diketogluconate present in the reaction mixture. Unreacted 2,5diketogluconate may then be recycled and subjected to further reduction reactions. It is intended that the specification and claims hereof be understood to include the above methods of practicing the present invention, as well as other procedures for carrying out the reduction which will be evident to those skilled in the art such as, but not limited to, conducting the reduction as either a batch or continuous process.

It will be understood that one mole of an amine-borane contains three equivalents of hydride ion. Thus, high yields of the desired 2-ketogulonate can be formed by employing between about 0.30 to about 0.40 moles, preferably about 0.33 moles, of an amine-borane per mole of 2,5-diketogluconate starting material present in the reaction mixture. However, since the 2-keto group of the product 2-ketogulonate is only very slowly reduced by excess amine-borane reducing agent, especially when $R_1$ and $R_2$ are both other than hydrogen, higher rates of reduction of the 5-keto group can be achieved, if desired, by use of relatively larger amounts of reducing agent, for example up to about 2 to 3 moles of amine-borane per mole of 2,5-diketogluconate and the use of such an excess ensures complete conversion of the 2,5-diketogluconate starting material in the reaction mixture. The amine-borane reducing agent can be added to the solution of the 2,5-diketogluconate either in one batch at the start of the reaction or in portions during the course of the reaction and may be added either as a solid or as a solution.

During the reduction of the 2,5-diketogluconate with the amine-borane the pH of the solution should be maintained at between about 2 and 7, preferably between about 4 and 6. To maintain the pH in the above range, an acid such as a mineral acid, for example hydrochloric acid, sulfuric acid, phosphoric acid and the like, or an organic acid such as a lower alkyl carboxylic acid, for example a $C_1$ to $C_6$ alkyl carboxylic acid, may be added to the reaction mixture. The pH of an aqueous solution of sodium or calcium 2,5-diketogluconate produced by fermentation is usually lower than 5 and such a solution is therefore suitable for use in the present reduction process.

The time necessary to complete the reduction will depend on the temperature and the amounts of reagents employed. However, generally reaction times will be relatively short with the reaction being substantially complete in periods of about 15 minutes to about 3 hours. On completion of the selective reduction any unreacted 2,5-diketogluconate can be recycled for further reaction or it can be effectively removed from the reaction mixture by heating with an acid or base followed by filtration.

The 2-ketogulonate formed in the above process can be isolated, together with lesser amounts of the 2-ketogluconate, by filtering the reaction mixture and adjusting the filtrate to a pH between about 1.5 and 2 by addition of an acid such as concentrated sulfuric acid and filtering off and discarding any precipitate that is formed. The desired product can be collected by removing the water or water-organic cosolvent, for example by freeze drying or heating under reduced pressure. The ratio of 2-ketogulonic acid to 2-ketogluconic acid in the mixture can be determined by gas-liquid chromatography of the pertrimethylsilylated methyl esters using a five foot OV-210 (Ohio Valley Specialty Co.) column at 135° C. However, other methods of analysis, for example liquid chromatography or thin layer chromatography, may be employed. The 2-ketogulonic acid formed in the present reduction process can readily be converted to ascorbic acid by means known in the art. The small amounts of 2-ketogluconate in the reaction mixture may be separated, for example by chromatography, and the 2-ketogulonate converted to ascorbic acid. However, the mixture of 2-ketogulonate containing small amounts of 2-ketogluconate can be used directly in the subsequent reaction, the 2-ketogluconate being converted to erythorbic acid, which can be separated from the ascorbic acid formed. Thus for example, the mixture of the 2-keto acids can be converted to the methyl esters by refluxing in methanol in the presence of an acid catalyst such as hydrochloric acid or a sulfonic ion exchange resin for about 3 to 24 hours. Other esters can be formed in this manner using the appropriate alcohol. The esters are formed directly when an alkyl ester of 2,5-diketogluconic acid is the starting material for the selective reduction. The mixture of methyl esters can be separated and is then refluxed in methanol in the presence of a base, such as sodium bicarbonate, in an inert atmosphere. On cooling, sodium ascorbate and sodium erythorbate precipitate out. The crude salts are collected by filtration, mixed with water and deionized with a cation exchange resin such as Dowex 50 (Dow Chemical Co.). The water is removed and ascorbic acid and erythrobic acid are recrystallized from methanol-water to give ascorbic acid containing small amounts of erythorbic acid. If desired, ascorbic acid may be obtained by recrystallization from, for example, a 4:1 methanol-water solution. Other suitable solvents or cosolvents can be employed if desired. If desired, the methyl esters of 2-ketogulonic acid and 2-ketogluconic acid can be separated and converted to ascorbic acid and erythorbic acid respectively using the same conditions as described above for the mixture of esters.

Ascorbic acid can also be prepared selectively from the 2-ketogulonate containing small amounts of the 2-ketogluconate obtained by the present reduction process by heating in a suitable organic solvent, such as benzene, toluene, xylene and the like, at about 50° C. to 130° C., preferably 60° C. to 90° C., in the presence of an acid selected from hydrochloric acid, hydrobromic acid, sulfuric acid and sulfonic ion exchange resins, although other similar acids may be used. A preferred acid is hydrochloric acid. After heating for a period of about 3 to 12 hours, depending on the reaction employed, lactonization of the 2-ketogulonate to ascorbic acid is substantially complete. In this process, erythorbic acid is not produced from the small amounts of 2-ketogluconate present and this method thereby affords a simple method of selectively forming ascorbic acid from the reaction product of the present amine-borane reduction.

The present invention is illustrated by the following examples. It should be understood, however, that the invention is not limited to the specific details of these examples.

EXAMPLE 1

To 100 ml of a 15% (w/v) aqueous solution of 2,5-diketogluconic acid at a temperature of 6°-8° C. and pH 3.0 was added 4.6 g (1.07 mole) of borane-dimethylamine complex. After 1 hour h.p.l.c. analysis (Aminex A-21 resin in formate form, ammonium formate buffer at pH 5.0) indicated complete reduction had occurred, whereupon 30 ml of acetone was added and the solution slowly poured into a slurry of 150 ml of Dowex 50 ion exchange resin (hydrogen form). After hydrogen evolution had ceased, the resin was removed by filtration, solvent removed via rotary evaporation and the residue placed in 200 ml of anhydrous methanol. Amberlyst 15 ion exchange resin catalyst (20ml, hydrogen form) was added and the methanol/trimethylborate azeotrope was distilled off at atmospheric pressure with concomitant esterification of the 2-ketogulonic acid. The methanol solution was filtered and reduced to 30 ml whereupon crystallization proceeded affording on isolation 6.9 g of methyl 2-ketogulonate (mp 152°-154° C., lit 153°-154° C.). The mother liquor was evaporated in vacuo to a solid containing 3.5 g of methyl-2-ketogulonate and methyl-2-ketogluconate in a ratio of 77:23 (by glpc analysis of the per-silylated methyl esters on a 5 ft OV-210 column at 135° C.), corresponding to an overall reduction stereoselectivity of 92:8, 2-ketogulonic:2-ketogluconic acids.

EXAMPLE 2

The procedure of Example 1 was repeated maintaining the pH at 3.5 with 6 N HCl. Analysis by hlpc (Dowex 50 ion exchange resin in the calcium form, 0.01 M $CaCl_2$ buffer at pH 8) after 3 hours at 0° C. showed both 2-ketogulonate and 2ketogluconate in a ratio of 94:6. The reaction was treated as described in Example 1 affording after esterification a 96:4 mixture (by glpc analysis) of methyl 2-ketogulonate and methyl 2-ketogluconate.

EXAMPLES 3-23

The reduction of sodium 2,5-diketogluconate was effected with a number of amine-boranes, under different temperature and pH conditions, by the following procedure: To a stirred solution of 10.5% (w/v) sodium 2,5-diketogluconate at specified temperature and pH is added the solid amine-borane in one portion. Reactions are followed for completeness by hplc analysis (Aminex-25 resin in formate form, ammonium formate buffer at pH 5.3) and yields determined by hplc analysis with internal standard based on hydride equivalents used. Ratios of 2-ketogulonic and 2-ketogluconic acids in Examples 3 through 20 were determined by conversion as described in Example 1 to the corresponding methyl esters and glpc analysis of their corresponding pertrimethylsilylated methyl esters. (5 ft OV-210 column at 135° C.) Ratios of 2-ketogulonic and 2-ketogluconic acids in Examples 21 through 23 were determined by conversion to ascorbic and erythorbic acids and analysis of their corresponding pertrimethylsilylated methyl esters by glpc analysis as previously described.

The results obtained were as follows:

| Example No. | Amine-Borane | Temp °C. | pH | Time (Hr) | (a)Reactant Ratio | % Yield | (b)Ratio of 2-keto acids |
|---|---|---|---|---|---|---|---|
| 3 | $(CH_3)_2NH \cdot BH_3$ | 0 | 5.0 | 1 | 0.33 | 59 | — |
| 4 | $C_5H_5N \cdot BH_3$ | 0 | 5.0 | 0.5 | 0.33 | 76 | — |
| 5 | $(CH_3)_3CNH_2 \cdot BH_3$ | 0 | 5.0 | 1.0 | 0.33 | 61 | — |
| 6 | $C_5H_5N \cdot BH_3$ | 0 | 5.0 | 0.5 | 0.33 | 76 | 88:12 |
| 7 | $C_5H_5N \cdot BH_3$ | 30 | 5.0 | — | 0.33 | 70 | — |
| 8 | $C_5H_5N \cdot BH_3$ | 70 | 5.0 | — | 0.33 | 59 | — |
| 9 | $(CH_3)_2NH \cdot BH_3$ | 0 | 5.0 | 1 | 0.33 | 59 | — |
| 10 | $(CH_3)_2NH \cdot BH_3$ | 0 | 5.0 | — | 0.33 | 62 | 86:14 |
| 11 | $(CH_3)_2NH \cdot BH_3$ | 0 | 5.0 | 1 | 0.28 | 94 | — |
| 12 | $(CH_3)_2NH \cdot BH_3$ | 0 | 3.9 | 0.75 | 0.28 | 84 | 92:8 |
| 13 | $(CH_3)_2NH \cdot BH_3$ | 0 | 2.0 | 2.0 | 1.00 | — | 90:10 |
| 14 | $(CH_3)_2NH \cdot BH_3$ | 0 | 3.0 | 2.0 | 1.00 | — | 87:13 |
| 15 | $(CH_3)_2NH \cdot BH_3$ | 0 | 4.0 | 2.0 | 1.00 | — | 87:15 |
| 16 | $(CH_3)_2NH \cdot BH_3$ | 0 | 5.0 | 2.0 | 1.00 | — | 87:13 |
| 17 | $(CH_3)_2NH \cdot BH_3$ | 0 | 5.0 | 2.0 | 0.50 | — | 86:14 |
| 18 | $(CH_3)_2NH \cdot BH_3$ | 0 | 5.0 | 2.0 | 0.33 | — | 86:14 |
| 19 | $C_5H_5N \cdot BH_3$ | 0 | 5.0 | 2.0 | 1.00 | — | 88:12 |
| 20 | $(CH_3)CNH_2 \cdot BH_3$ | 0 | 5.0 | 2.0 | 1.00 | — | 88:12 |
| 21 | $C_5H_5N \cdot BH_3$ | 0 | 5.0 | 5.5 | 0.33 | 79 | 92:8 |
| 22 | $(CH_3)_2NH \cdot BH_3$ | 0 | 5.0 | 2.5 | 0.33 | 83 | 92:8 |
| 23 | $(CH_3)_2NH \cdot BH_3$ | 0 | 5.0 | 1.5 | 0.33 | 84 | 89:11 |

(a)Reactant ratio = moles of amine borane/moles of 2,5-diketogluconate
(b)Ratio of 2-keto acids = moles of 2-ketogulonate:moles of 2-ketogluconate

I claim:
1. A process for the preparation of a 2-ketogulonate which comprises reducing a 2,5-diketogluconate with an amine-borane selected from those of the formula $R_1R_2HN.BH_3$ and pyridine-borane in solution at a pH between about 2 and 7 at a temperature between about −20° to 70° C., wherein $R_1$ and $R_2$, are each selected from hydrogen and alkyl of 1 to 4 carbon atoms; and said 2,5-diketogluconate is selected from 2,5-diketogluconic acid, a normal alkyl ester of said acid wherein said alkyl group is of 1 to 4 carbon atoms, and a salt of said acid having a counterion selected from an alkali metal, an alkaline earth metal, ammonium and tetraalkylammonium having from 1 to 4 carbon atoms in each alkyl group.

2. A process according to claim 1 wherein said amine-borane is of the formula $R_1R_2HN.BH_3$.

3. A process according to claim 2, wherein $R_1$ and $R_2$ are each hydrogen.

4. A process according to claim 2, wherein $R_1$ and $R_2$ are each methyl.

5. A process according to claim 2, wherein $R_1$ is t-butyl and $R_2$ is hydrogen.

6. A process according to claim 1, wherein said amine-borane is pyridine-borane.

7. A process according to claim 1 wherein the temperature is between 0° and 25° C.

8. A process according to claim 1 wherein between about 0.30 and 0.40 moles of said amine-borane is employed.

9. A process according to claim 1 wherein the pH is between about 4 and 6.

10. A process according to claim 1 wherein the 2,5-diketogluconate is sodium 2,5-diketogluconate.

11. A process according to claim 1 wherein the 2,5-diketogluconate is calcium 2,5-diketogluconate.

12. A process according to claim 1 wherein the 2,5-diketogluconate is methyl 2,5-diketogluconate.

13. A process according to claim 1 wherein the reduction is effected in aqueous solution.

14. A process according to claim 13 wherein said aqueous solution contains a co-solvent selected from an alkanol of 1 to 4 carbon atoms and an alkanediol of 2 to 4 carbon atoms.

15. A process according to claim 14 wherein said co-solvent is methanol.

16. A process according to claim 15 wherein the 2,5-diketogluconate is between about 5 and 20 weight percent of said solution.

* * * * *